(12) United States Patent
Wulffhart et al.

(10) Patent No.: US 6,455,028 B1
(45) Date of Patent: Sep. 24, 2002

(54) IPRATROPIUM FORMULATION FOR PULMONARY INHALATION

(75) Inventors: Harold Wulffhart, Northyork (CA); Khaldoun Ayoub, Richmond Hill (CA); Rosemary Logiudice, Woodbridge (CA); Hanna Piskorz, Richmond Hill (CA)

(73) Assignee: Pharmascience, Montreal (CA)

(*) Notice: Subject to any disclaimer, the term of this patent is extended or adjusted under 35 U.S.C. 154(b) by 0 days.

(21) Appl. No.: 09/841,181

(22) Filed: Apr. 23, 2001

(51) Int. Cl.[7] .............................. A61K 9/12; A61K 9/14
(52) U.S. Cl. .......................... 424/45; 424/46; 424/489; 424/434; 424/435
(58) Field of Search .......................... 424/45, 46, 489, 424/434, 435

(56) References Cited

U.S. PATENT DOCUMENTS

| | | |
|---|---|---|
| 3,505,337 A | 4/1970 | Zeile et al. |
| 4,385,048 A | 5/1983 | Mygind et al. |
| 5,126,123 A | 6/1992 | Johnson |
| 5,182,097 A | 1/1993 | Byron et al. |
| 5,225,183 A | 7/1993 | Purewal et al. |
| 5,427,282 A | 6/1995 | Greenleaf et al. |
| 5,603,918 A | 2/1997 | McNamara |
| 5,683,676 A | 11/1997 | Akehurst et al. |
| 5,874,063 A | 2/1999 | Briggner et al. |
| 5,910,301 A | 6/1999 | Farr et al. |
| 5,955,058 A | 9/1999 | Jager et al. |
| 6,299,861 B1 * | 10/2001 | Banholzer et al. ............ 424/45 |

FOREIGN PATENT DOCUMENTS

| | | |
|---|---|---|
| WO | WO 93/11743 | 6/1993 |
| WO | WO 93/11744 | 6/1993 |
| WO | WO 93/11745 | 6/1993 |
| WO | WO 93/15741 | 8/1993 |
| WO | WO 94/03153 | 2/1994 |
| WO | WO 96/18384 | 6/1996 |
| WO | WO 96/32099 | 10/1996 |
| WO | WO 96/32150 | 10/1996 |
| WO | WO 96/32151 | 10/1996 |

OTHER PUBLICATIONS

Boehringer Ingelheim, Drug Information on Combivent®, Feb. 1999 (obtained through on–line PDR).*
Dellamary et al. (2000), "Hollow Porous Particles in Metered Dose Inhalers," *Pharm. Res.* 17(2):168–174.

* cited by examiner

Primary Examiner—José G. Dees
Assistant Examiner—Mina Haghighatian
(74) Attorney, Agent, or Firm—Reed & Associates

(57) ABSTRACT

Pharmaceutical aerosol formulations are provided comprising substantially nonacicular particles of a bronchodilator selected from the group consisting of ipratropium and pharmacologically acceptable salts, solvates, hydrates, esters and isomers thereof. The described formulations include a propellant selected from the group consisting of a fluorocarbon propellant, a hydrogen-containing fluorocarbon propellant, and mixtures thereof. The formulations are substantially free of both surfactant and solvent. Methods of use and drug delivery devices are also provided.

67 Claims, No Drawings

IPRATROPIUM FORMULATION FOR PULMONARY INHALATION

TECHNICAL FIELD

The invention relates generally to pharmaceutical formulations, and more particularly relates to pharmaceutical formulations comprising a bronchodilator. In addition, the invention relates to methods for treating patients using the formulations and drug delivery devices for delivering the formulations.

BACKGROUND

Administration of pharmacologically active agents to the lungs of a patient offers many advantages over other modes of drug administration, e.g., oral administration of a tablet or capsule, transdermal administration of an active agent, and the like. Administration of a drug to the lungs provides for increased onset of action, decreased first-pass effect, reduced degradation in the gastrointestinal milieu, minimized side effects, and titrated doses. Conventional means to deliver the active agent to the lungs of a patient include administration of an aerosol formulation containing the active agent from, for example, a manual pump spray or pressurized metered-dose inhaler.

Often, the active agent is dissolved, suspended or emulsified in a mixture of a solvent, surfactant and propellant. The mixture is maintained under pressure in a canister that has been sealed with a metering valve. The canister, in turn, is fitted into a suitable actuator housing adapted to hold the canister. The entire assembly, e.g., canister with valve, actuator housing, formulation, etc., serves as a drug delivery device suitable for pulmonary administration of the pharmaceutical formulation.

When administering the drug, the patient must actuate the drug delivery device. The actuation releases a fraction of the formulation from within the canister to the external environment. A force, created by vaporized propellant, expels the drug into the air and away from the device. The patient then inhales the aerosolized drug. The metering valve controls the amount of the formulation released, which, in turn, effectively controls the amount of drug available for inhalation by the patient.

Traditionally, chlorofluorocarbons (CFCs) have been used as propellants in aerosol formulations. Although CFCs are effective propellants, controversy has surrounded their use due to their suspected ozone-depleting effects. Essentially, degradation of CFCs in the upper atmosphere produces chloride radicals that react with, and deplete, ozone. As a consequence, alternative formulations are desired that include propellants having the effectiveness of CFCs, yet without their ozone-depleting effects.

The introduction of fluorocarbons and hydrogen-containing fluorocarbons as propellants in aerosol formulations addressed many of the environmental concerns associated with conventional CFC propellants. Although fluorocarbon and hydrogen-containing fluorocarbon compounds have sufficient vapor pressures for use as propellants, the transition to the new propellants has been difficult. Largely, the problem rests with the poor solvency associated with fluorocarbon and hydrogen-containing fluorocarbon propellants. Dellamary et al. (2000) *Pharm. Res.* 17(2):168–174. As a consequence, many formulations containing fluorocarbon and hydrogen-containing fluorocarbon propellants require the presence of cosolvents and/or surfactants. See WO 93/11745. Among other drawbacks, these components increase the cost of the final formulation and may impart an unpleasant taste, trigger an asthmatic attack or have other undesirable effects on the patient.

Nevertheless, some researchers have described formulations that do not require the use of any surfactant or cosolvent. For example, WO 93/11743 describes formulations containing a fluorocarbon or hydrogen-containing fluorocarbon propellant in combination with salmeterol, salbutamol, fluticasone propionate, or beclomethasone dipropionate. Further, WO 93/11744 describes formulations containing a fluorocarbon or hydrocarbon-containing fluorocarbon propellant that are free of any surfactants and may be used with nearly any drug. However, such formulations are unsatisfactory for some drugs, particularly ipratropium bromide.

Ipratropium bromide has been described in U.S. Pat. No. 3,505,337 to Zeile et al. as a stomach acid secretion inhibitor.

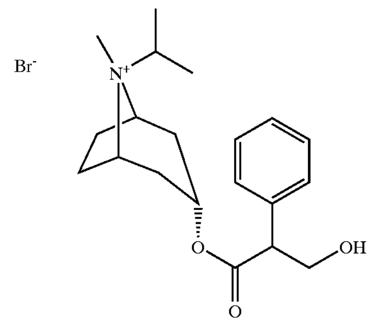

IPRATROPIUM BROMIDE

Ipratropium Bromide (±)-3-(3-Hydroxyl-1-oxo-2-phenylpropoxy)-8-methyl-8-(1-methylethyl)-8-azoniabicyclo[3.2.1] octane Bromide Thereafter, it was recognized that the drug's anticholinergic effects would be advantageous in the treatment of patients requiring bronchodilator therapy. Gross et al. (1984) *Am. Rev. Respir. Dis.* 129(5):856–870. Ipratropium bromide as an inhalation aerosol is commercially available as ATROVENT® (Boehringer Ingelheim Pharmaceuticals, Inc., Ridgefield, Conn.). The formulations, however, use the CFC propellants trichloromonofluoromethane (CFC-11), dichlorodifluoromethane (CFC-12) and dichlorotetrafluoroethane (CFC-114).

Aerosol formulations of ipratropium bromide using fluorocarbon and hydrogen-containing fluorocarbon propellants have also been proposed. For example, U.S. Pat. No. 5,225,183 to Purewal et al. describes aerosol formulations of ipratropium bromide having a hydrogen-containing fluorocarbon propellant that is substantially free of CFCs. The described formulations, however, require a surface-active agent, i.e., surfactant, to stabilize the formulation or lubricate a valve stem when used in conjunction with an inhaler.

Furthermore, aerosol formulations containing ipratropium bromide without CFC propellants and without surfactants and solvents have been tried, but were demonstrated to be unsatisfactory for use in conventional metered-dose inhalers. Specifically, applicants found that crystalline ipratropium, due to its acicular, i.e., needle-like shape, tended to cause aggregation in these formulations, thereby clogging the delivery valve and possibly other components of the inhaler as well.

There is, accordingly, a need in the art to provide an aerosol formulation comprising a fluorocarbon or hydrogen-containing fluorocarbon propellant or mixture thereof in combination with ipratropium as an active agent that is readily used with conventional metered-dose inhalers. The present invention addresses both this and other needs by providing a fluorocarbon or hydrogen-containing fluorocarbon aerosol formulation that forms little or no aggregates upon repeated actuation. Specifically, it has been found that by using ipratropium particles having a certain size and morphology, an aerosol formulation can be made that is free of CFC propellants and does not clog the valve of a drug delivery device.

SUMMARY OF THE INVENTION

Accordingly, it is a primary object of the invention to provide a pharmaceutical aerosol formulation comprising substantially nonacicular particles (or particles treated in a such a manner to render usable) of a bronchodilator selected from the group consisting of ipratropium and pharmacologically acceptable salts, solvates, hydrates, esters and isomers thereof and a propellant selected from the group consisting of a perfluorocarbon propellant, a hydrogen-containing fluorocarbon propellant, and mixtures thereof, wherein the formulation is substantially free of both surfactant and solvent.

It is another object of the invention to provide such a formulation wherein the substantially nonacicular particles are substantially spherical.

It is a further another object of the invention to provide such a formulation wherein the bronchodilator is a pharmacologically acceptable salt of ipratropium.

It is a still another object of the invention to provide such a formulation wherein the particles of the active agent have an average particle size in the range of about 0.5 $\mu$m to about 10 $\mu$m.

It is a further object of the invention to provide such a formulation wherein the propellant is selected from the group consisting of $CHF_2CHF_2$, $CF_3CH_2F$, $CHF_2CH_3$, $CF_3CHFCF_3$, $CF_3CF_3$, $CF_3CF_2CF_3$ and mixtures thereof.

Another object of the invention is to provide a method for treating a patient suffering from a condition that is responsive to treatment with an aerosol formulation of a bronchodilator by administering to the patient, via inhalation, a formulation as provided herein.

Still another object of the invention is to provide a drug delivery device for pulmonary administration of a pharmaceutical formulation as provided herein.

It is a further object of the invention to provide such a drug delivery device wherein the device is a metered-dose inhaler.

Additional objects, advantages and novel features of the invention will be set forth in the description that follows, and in part will become apparent to those skilled in the art upon examination of the following, or may be learned by practice of the invention.

In one embodiment, a pharmaceutical aerosol formulation is provided comprising substantially nonacicular particles of a bronchodilator selected from the group consisting of ipratropium and pharmacologically acceptable salts, solvates, hydrates, esters and isomers thereof and a propellant selected from the group consisting of a perfluorocarbon propellant, a hydrogen-containing fluorocarbon propellant, and mixtures thereof. Nonacicular particles are particles that are not needle-shaped. Preferably, the substantially nonacicular particles in the formulation are substantially spherical in shape.

In addition, the formulation is substantially free of both surfactant and solvent. A formulation is "substantially free" of both surfactant and solvent when less than 1% wt./wt. (based on the propellant), preferably less than 0.5% wt./wt., and most preferably less than 0.1% wt./wt. of surfactant and/or solvent is present in the formulation. Optimally, however, the formulation is completely free of both surfactant and solvent.

Although any salt, solvate, ester or isomer of ipratropium may serve as an active agent, ipratropium bromide is particularly preferred. In addition, although any perfluorocarbon or hydrogen-containing fluorocarbon propellant may be used, preferred propellants are 1,1,1,2-tetrafluoroethane ($CF_3CHF_2$), 1,1,1,2,3,3,3-heptafluoro-n-propane ($CF_3CHFCF_3$) and mixtures thereof, with 1,1,1,2-tetrafluoroethane ($CF_3CHF_2$) being particular preferred.

The substantially nonacicular particles of the active agent may be of any size suitable for pulmonary administration. It is preferred however, that the substantially nonacicular particles of the bronchodilator have a particle size of about 0.5 $\mu$m to about 10 $\mu$m, more preferably about 1 $\mu$m to about 7.5 $\mu$m, and most preferably about 1 $\mu$m to about 5 $\mu$m.

In another embodiment, a method is provided for treating a patient suffering from a condition that is responsive to treatment with pulmonary administration of a bronchodilator, involving administering to the patient, via inhalation, a pharmaceutical formulation as described herein. The formulations are particularly suited to treat a patient suffering from asthma or other conditions that require bronchodilation.

In yet another embodiment, a drug delivery device is provided comprising a pharmaceutical formulation as described herein. The drug delivery device may be any conventional device designed to administer a pressurized aerosol formulation to the lungs. A particularly preferred drug delivery device is a metered-dose inhaler.

DETAILED DESCRIPTION OF THE INVENTION

Before describing the present invention in detail, it is to be understood that this invention is not limited to particular propellants, drug delivery devices and the like, as such may vary. It is also to be understood that the terminology used herein is for describing particular embodiments only, and is not intended to be limiting.

It must be noted that, as used in this specification and the appended claims, the singular forms "a," "an" and "the" include plural referents unless the context clearly dictates otherwise. Thus, for example, reference to "a propellant" includes a single propellant as well as two or more different propellants, reference to an "active agent" refers to a single active agent or to combinations of two or more active agents, and the like.

In describing and claiming the present invention, the following terminology will be used in accordance with the definitions set forth below.

The terms "active agent," "drug" and "pharmaceutically active agent" are used interchangeably herein to refer to a chemical material or compound which, when administered to an organism (human or animal) induces a desired pharmacologic effect. Included are derivatives and analogs of those compounds or classes of compounds specifically mentioned that also induce the desired pharmacologic effect.

By "pharmaceutically acceptable carrier" is meant a material or materials that are suitable for pulmonary drug administration to an individual along with an active agent without causing any undesirable biological effects or interacting in a deleterious manner with any of the other components of the pharmaceutical formulation in which it is contained. Generally, the pharmaceutically acceptable carrier is a propellant, although other carriers, such as water, carbon dioxide, nitrogen, compressed air, or combination thereof, may be used.

Similarly, a "pharmacologically acceptable" salt, solvate, hydrate, ester, isomer or other derivative of an active agent as provided herein is a salt ester, solvate, hydrate, isomer or other derivative that is not biologically or otherwise undesirable.

The term "aspect ratio" is used herein in its conventional sense to refer to the ratio of the longest dimension to the shortest dimension of a particle. For example, a perfect sphere has an aspect ratio of 1:1 (or 1). A perfect cube has an aspect ratio of about 1.73:1 (the distance between two farthest vertices in the cube verses to the length of a side of the cube).

By the terms "effective amount" or "therapeutically effective amount" of an active agent as provided herein are meant a nontoxic but sufficient amount of the agent to provide the desired therapeutic effect. The exact amount required will vary from subject to subject, depending on the age, weight, and general condition of the subject, the severity of the condition being treated, the judgment of the clinician, and the like. Thus, it is not possible to specify an exact "effective amount." However, an appropriate "effective amount" in any individual case may be determined by one of ordinary skill in the art using only routine experimentation.

The terms "treating" and "treatment" as used herein refer to reduction in severity and/or frequency of symptoms and/or their underlying cause, and improvement or remediation of damage. Thus, for example, the present method of "treating" asthma, as the term "treating" is used herein, encompasses both prevention of asthma in a predisposed individual and treatment of asthma in a clinically symptomatic individual.

The terms "condition," "disease" and "disorder" are used interchangeably herein as referring to a physiological state that can be prevented or treated by administration of a pharmaceutical formulation as described herein.

The term "patient" as in treatment of "a patient" refers to a mammalian individual afflicted with or prone to a condition, disease or disorder as specified herein, and includes both humans and animals.

The term "pulmonary" as used herein refers to any part, tissue or organ that is directly or indirectly involved with gas exchange, i.e., $O_2/CO_2$ exchange, within a patient. "Pulmonary" contemplates both the upper and lower airway passages and includes, for example, the mouth, nose, pharynx, oropharynx, laryngopharynx, larynx, trachea, carina, bronchi, bronchioles and alveoli. Thus, the phrase "pulmonary administration" refers to administering the formulations described herein to any part, tissue or organ that is directly or indirectly involved with gas exchange within a patient.

Formulations

The active agent in the formulation is a bronchodilator selected from the group consisting of ipratropium and pharmacologically acceptable salts, solvates, hydrates, esters and isomers thereof. It is preferred that a salt form of ipratropium is present in the formulation. Preferred salts of ipratropium include the chloride, bromide, and iodide salts, with the bromide salt being most preferred.

The active agent may be prepared according to the method presented in Zeile et al., supra. As described therein, the active agent may be prepared by reacting N-substituted noratropine with an alkylating agent, such as methylbromide. Alternatively, the active agent can be obtained through commercial sources. For example, ipratropium bromide can be purchased from Sigma, Inc., St. Louis, Mo. (product number 11637). Converting the quaternary salt of ipratropium into salts of other anions can be achieved by double decomposition as described in Zeile et al., supra.

Additional active agents may also be present in the formulations. Particularly preferred classes of additional active agents include anti-inflammatory steroids and additional bronchodilators.

Preferred anti-inflammatory steroids include, but are not limited to, those selected from the group consisting of beclomethasone, budesonide, cortisone, dexamethasone, flunisolide, hydrocortisone, prednisolone, prednisone, triamcinolone, pharmacologically acceptable salts thereof and combinations thereof.

An additional bronchodilator is optionally included in the formulations. Preferred additional bronchodilators include adrenaline, albuterol, aminophylline, bitolterol, dyphylline, ephedrine, fenoterol, formoterol, isoetharine, isoproterenol, isoprenaline, metaproterenol, oxtriphylline, phenylephrine, pentoxifylline, pirbuterol, reproterol, rimiterol, salmeterol, theophylline, terbutaline, tolubuterol, orciprenaline, pharmacologically acceptable salts thereof and combinations thereof. A particularly preferred second bronchodilator in the formulation is albuterol, preferably albuterol sulfate.

Salts, esters and derivatives of the active agent may be prepared using standard procedures known to those skilled in the art of synthetic organic chemistry and described, for example, by J. March, "Advanced Organic Chemistry: Reactions, Mechanisms and Structure," 4th Ed. (New York: Wiley-Interscience, 1992). For example, acid addition salts are prepared from the free base (e.g., compounds having a neutral —$NH_2$ or cyclic amine group) using conventional means, involving reaction with a suitable acid. Typically, the base form of an active agent is dissolved in a polar organic solvent such as methanol or ethanol and the acid is added at a temperature of about 0° C. to about 100° C., preferably at ambient temperature. The resulting salt either precipitates or may be brought out of solution by addition of a less polar solvent. Suitable acids for preparing the acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like as well as inorganic acids, e.g., hydrochloric acid, hydrobromic acid, sulfuric acid, nitric acid, phosphoric acid, and the like. An acid addition salt may be reconverted into the free base by treatment with a suitable base. Basic addition salts of an active agent having an acid moiety (e.g., carboxylic acid group or hydroxyl group) are prepared in a similar manner using a pharmaceutically acceptable base. Suitable bases include both inorganic bases, e.g., sodium hydroxide, potassium hydroxide, ammonium hydroxide, calcium hydroxide, magnesium hydroxide, and the like, as well as organic bases such as trimethylamine, or the like. Preparation of esters involves functionalization of hydroxyl and/or carboxyl groups that may be present within the molecular structure of the drug. The esters are typically acyl-substituted derivatives of free alcohol groups, i.e., moieties that are derived from carboxylic acids of the formula RCOOH where R is alkyl, and preferably is lower, i.e., $C_1$ to $C_6$, alkyl. Esters can be reconverted to the free acids, if desired, by using conventional hydrogenolysis or hydrolysis procedures. Preparation of amides and prodrugs can be carried out in an analogous manner. Other derivatives of the active agents may be prepared using standard techniques known to those skilled in the art of synthetic organic chemistry, or may be deduced by reference to the pertinent literature and texts.

Stereoisomers of the active agent are also included as part of the formulations described herein. A stereoisomer is a compound having the same molecular weight, chemical composition, and constitution as another, but with the atoms arranged differently. That is, certain identical chemical moieties are at different orientations in space. This difference has the consequence of rotating the plane of polarized light. A pair of stereoisomers that are mirror images of each other, but wherein the mirror images are nonsuperimposable on each other, are defined as enantiomers. Individual stereoisomers or enantiomers may have unique or beneficial properties that make that individual isomer particularly suited for the present invention. Consequently, individual stereoisomers or enantiomers and mixtures thereof of the active agents are included as part of the invention. Thus, each active agent may be present in the formulation as a racemate, i.e., or in enantiomerically pure form, e.g., as dextrorotatory ipratropium bromide or levorotatory ipratropium bromide, or as a mixture of nonequal amounts of each enantiomer, e.g., nonequal amounts dextrorotatory ipratropium bromide/levorotatory ipratropium bromide.

The various hydrates of the active agent(s) may also be used in the formulations of the invention. As is well known, one or more water molecules may associate with a particular compound through hydrogen bonding. Methods of producing hydrated species are known and include, for example, placing the active agent in a humid environment. In addition, methods of removing one or more water molecules are known and include, by way of example, exposing the active agent to dry heat. Preferably, when the active agent is ipratropium bromide, the monohydrate form is used.

Because of its acicular crystal form, ipratropium bromide, and other salts of ipratropium that have similarly shaped crystalline forms, must be processed into substantially nonacicular or other morphologically acceptable particles so that the valve and other components of the drug delivery device do not clog. Converting the needle-shaped crystals of ipratropium into substantially nonacicular particles minimizes aggregation, thereby reducing the tendency of the active agent to clog the valve and other components of the drug delivery device. "Substantially nonacicular" particles for purposes of the present invention are particles that will not aggregate to a degree such that a component, e.g., a valve, of a metered-dose inhaler will become clogged after repeated actuation. "Substantially nonacicular" particles include those particles that result from micronizing or "chopping up" acicular particles. Particularly preferred nonacicular particles are substantially spherical particles. Again, substantially spherical particles are particles sufficiently spherical in shape so as to not aggregate to a degree such that a component, e.g., a valve, of a metered-dose inhaler will become clogged after repeated actuation. The particles need not be perfectly uniform and regular, e.g., perfect spherical symmetry. Rather, the particles must only be substantially nonacicular in shape. Generally, substantially nonacicular particles as defined herein will have an aspect ratio of less than 4:1, preferably less than 2:1.

Devices and methods for producing substantially nonacicular particles from acicular and similarly shaped particles are well known in the art. The substantially nonacicular particles can be obtained by, for example, using the techniques of micronization, spheronization, the application of supercritical fluid technology or a combination these techniques. As will be appreciated by those skilled in the art, the following processes can be performed alone or in combination to produce the desired particles. Of course, additional techniques for producing substantially nonacicular particles may be used as well.

Micronization techniques involve placing bulk drug into a suitable mill. Such mills are commercially available from, for example, DT Industries, Bristol, Pa., under the tradename STOKES®. Briefly, the bulk drug is placed in an enclosed cavity and subjected to mechanical forces from moving internal parts, e.g., plates, blades, hammers, balls, pebbles, and so forth. Alternatively, or in addition to parts striking the bulk drug, the housing enclosing the cavity may turn or rotate such that the bulk drug is forced against the moving parts. Some mills, e.g., air-jet mills, include a high-pressure air stream that forces the bulk powder into the air within the enclosed cavity for contact against internal parts. Once the size and shape of the drug is achieved, the process may be stopped and drug having the appropriate size and shape is recovered. Generally, however, particles having the desired particle size range are recovered on a continuous basis by elutriation.

Spheronization involves the formation of substantially spherical particles and is well known in the art. Commercially available machines for spheronizing drugs are known and include, for example, Marumerizer™ from LCI Corp. (Charlotte, N.C.) and CF-Granulator from Vector Corp. (Marion, Iowa). Briefly, such machines include an enclosed cavity with a discharge port, a circular plate and a means to turn the plate, e.g., a motor. Bulk drug or moist granules of drug from a mixer/granulator are fed onto the spinning plate, which forces them against the inside wall of the enclosed cavity. The process results in drug particles having a spherical size. An alternative approach to spheronization that may be used includes the use of spray drying under controlled conditions. The conditions necessary to spheronize particles using spray-drying techniques are known to those skilled in the art and described in the relevant references and texts, e.g., *Remington: The Science and Practice of Pharmacy*, Twentieth Edition (Easton, Pa.: Mack Publishing Co., 2000).

Supercritical fluid technology uses methods that enable controlled formation of uniform particles having a substantially nonacicular shape using supercritical fluids. Such methods are known and described in the art. See, for example, U.S. Pat. Nos. 6,063,138 and 5,851,453 to Hanna et al. Briefly, a supercritical fluid is a material, e.g., carbon dioxide, held above a critical pressure and temperature, thereby resulting in a single phase. A solution containing the drug is mixed with supercritical fluid. The solvent from the drug solution is dispersed in the supercritical fluid. Under controlled conditions above the critical pressure and temperature of the supercritical conditions, dry, solvent-free particles can be recovered from the supercritical fluid. By controlling a number of factors, e.g., pressure, temperature, the supercritical fluid, etc., particles of a desired size and shape, e.g., spherical, precipitate out of the supercritical fluid.

To ensure that the drug particles have the proper size and shape, the particles may be analyzed using known techniques for determining particle morphology. For example, the particles can be visually inspected under a microscope and/or passed through a mesh screen. Preferred techniques for visualization of particles include scanning electron microscopy (SEM) and transmission electron microscopy (TEM). Particle size analysis may take place using laser diffraction methods. Commercially available systems for carrying out particle size analysis by laser diffraction are available from Clausthal-Zellerfeld, Germany (HELOS H1006).

The substantially nonacicular particles of the active agent are a suitable size for pulmonary administration. The particles will preferably have an average particle size in the range of about 0.5 μm to about 10 μm, more preferably in the range of about 1 μm to about 7.5 μm, and most preferably in the range of about 1 μm to about 5 μm. Preferably, greater than about 85%, more preferably greater than about 95%, and most preferably greater than about 98% of the population of particles in the formulation will fall within the desired particle size range, e.g., about 0.5 μm to about 10 μm, about 1 μm to about 7.5 μm, and so on.

The formulations also include a pharmaceutically acceptable propellant that is not a CFC. The propellant may be any perfluorocarbon propellant, hydrogen-containing fluorocarbon propellant or mixture thereof. Preferred perfluorocarbon propellants include, without limitation, $CF_3CF_3$ and $CF_3CF_2CF_3$. Preferred hydrogen-containing fluorocarbon propellants include, without limitation, $C_{1-4}$ hydrogen-containing fluorocarbons such as $CHF_2CHF_2$, $CF_3CH_2F$, $CHF_2CH_3$ and $CF_3CHFCF_3$. The mixture may be comprised of two, three, four or more perfluorocarbon and/or hydrogen-containing fluorocarbon propellants. A mixture of propellants, when present, will preferably be comprised of only two propellants. Single propellants, e.g., 1,1,1,2-tetrafluoroethane ($CF_3CHF_2$), may also be used. Preferred formulations include one or more hydrogen-containing fluorocarbon propellants. In particular, it is preferred that the hydrogen-containing fluorocarbon propellant is selected from the group consisting of 1,1,1,2-tetrafluoroethane ($CF_3CHF_2$), 1,1,1,2,3,3,3-heptafluoro-n-propane ($CF_3CHFCF_3$) and mixtures thereof.

The propellant is preferably present in an amount greater than 95% wt./wt., more preferably greater the 98% wt./wt., and most preferably greater than 99% wt./wt. of the total formulation. The active agent will preferably represent less than 2% wt./wt., more preferably less than 1% wt./wt., and most preferably less than 0.5% wt./wt. of the total formulation.

As stated previously, the formulations are substantially free of both surfactant and solvent. Preferably, the formulations are completely free of both surfactant and solvent. Thus, for example, the formulations are free or substantially free of solvents such as aliphalic alcohols and polyols such as ethanol, isopropanol, and propylene glycol. Volatile solvents, e.g., saturated hydrocarbons such as propane, n-butane, isobutane, pentane and alkyl ethers, are also absent. Also omitted or substantially omitted from the formulation are surfactants such as oleic acid, sorbitan trioleate, sorbitan mono-oleate, sorbitan monolaurate, polyoxyethylene (2) sorbitan monolaurate, lecithin, oleyl polyoxyethylene (4) ether, stearyl polyoxyethylene (2) ether, lauryl polyoxyethylene (4) ether, block copolymers of oxythylene and oxypropylene, diethylene glycol dioleate, tetrahydrofurfuryl oleate, ethyl oleate, isopropyl myristate, glyceryl mono-oleate, glyceryl monostearate, glyceryl monoricinoleate, cetyl alcohol, stearyl alcohol, polyethylene glycol, cetyl pyridinium chloride, benzalkonium chloride, olive oil, glyceryl monolaurate, corn oil, cotton seed oil and sunflower oil. For purposes of the present invention, a formulation is "substantially free" of both surfactant and solvent when less than 1% wt./wt. (based on the propellant), preferably less than 0.5% wt./wt., and most preferably less than 0.1% wt./wt. of surfactant and/or solvent is present in the formulation.

The formulations may have one or more excipients in addition to the active agent and propellant. The additional excipient(s), however, must not be a solvent or surfactant and must be pharmaceutically acceptable. Thus, for example, excipients such as buffers (e.g., organic phosphates), acidifying agents (e.g., citric acid), tonicity agents (e.g., sodium chloride and dextrose), lubricants, and the like can be present in the formulation. Specific examples of each of these excipients are well known by those skilled in the art of pharmaceutical formulation.

Drug Delivery Devices

Drug delivery devices for delivering the aerosol formulations of the present invention are also provided. The drug delivery device comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister The canister may be made of any suitable material such as aluminum, aluminum alloys, stainless steel, tin, plastic or glass. Canisters comprising aluminum, however, are preferred. Once a valve is crimped into place, the canisters must be able to adequately seal the propellant without leaking. Optionally, the interior of the canister may be anodized or laminated with a polymer or plastic coating. For example, a polymer coating may include, for example, fluorocarbon polymers based on tetrafluoroethylene (PTFE), fluorinated ethylene propylene (FEP), perfluoroalkoxyalkane (PFA), ethylene tetrafluoroethylene (ETFE), poly(vinyldiene fluoride) (PVDF), chlorinated ethylene tetrafluoroethylene, and combinations thereof. Furthermore, these polymers may be blended with nonfluorinated polymers such as, for example, polyamides, polyimides, polyethersulfones, polyphenylene sulfides, amine-thermosetting resins, and combinations thereof. See, for example, WO 96/32099 for a discussion of polymer coatings used on the internal surfaces of canisters used in metered-dose inhalers.

The canister is fitted with a valve, preferably a metering valve. Metering valves deliver a specific amount of the formulation each time the device is actuated. Preferably, a gasket will also be used between the valve and the canister to prevent leakage of the formulation. Gaskets that are used in the device may be composed of any suitable material such as, for example, polyethylene, chlorobutyl, rubber, or neoprene. Suitable valves are available commercially and may be obtained from, for example, Valois Pharm., Marly-le-Roi, France (under the product codes DF10, DF30 and DF60), Bespak Inc., Apex, N.C. (under the product codes BK300, BK356, BK357, BK 700), and 3M Corp., St. Paul, Minn. (under the product code A66172).

The formulation may be placed in the canister under a cold-filling process. In this process, the propellant is cooled to a temperature such that the propellant exists as a liquid. This temperature is around −40° C. or below. The liquefied propellant is placed in the canister followed by the addition of the active agent and any other excipient(s). The propellant, active agent and optional excipient(s) are mixed together followed by the addition of the valve. The valve is secured into place by crimping such that the canister is airtight.

Alternatively, a process known as "back filling" may be used to fill the canister. In this process, the formulation is added to a capped canister through the metering valve from a bulk reservoir. In one version, an aliquot is taken from a reservoir containing the formulation and filled into the canister through the valve. In another version, the active agent and propellant are stored separately and either simultaneously or sequentially filled into the canister through the valve. The active can also be added as a powder to the canister, the valve crimped into position and the propellant dosed through the can.

The canisters are filled leaving a sufficient "head space" or volume not filled with liquid. Among other purposes, such a space ensures that shaking the canister will thoroughly mix the formulation. Canisters containing a conventional aerosol formulation often use a head space representing about 10% of the total volume of the canister. When placed in a sealed canister, the formulations described herein are filled so as to leave a head space representing greater than about 15%, more preferably greater than about 20%, and still more preferably greater than about 40% of the overall volume of the sealed canister. Most preferably the head space will represent greater than about 60% of the overall volume of the canister. About 98% represents the maximum amount of head space suitable for a canister containing a formulation described herein. Although not wishing to be bound by theory, it is believed that the relatively less dense nature of the formulation requires a relatively greater amount of head space.

The filled canisters are then placed in a suitable housing to complete the drug delivery device. The housing generally includes a sleeve conforming to the shape of the canister. The sleeve allows for the canister to be slid relative to the housing. In addition, the housing also includes a cylindrical passage that is operatively connected to the metering valve on the canister. Thus, in operation, when the canister is moved relative to the housing such that the metering valve is depressed, a fixed amount of formulation is released initially through the metering valve and then though the cylindrical passage of the housing. As the propellant vaporizes, the drug is suspended in air. Patients then inhale the suspended drug, thereby effecting pulmonary drug administration.

Preferred drug delivery devices are metered-dose inhalers. Metered-dose inhalers are described in Remington: *The Science and Practice of Pharmacy,* Twentieth Edition (Easton, Pa.: Mack Publishing Co., 2000) and in Ansel et al., *Pharmaceutical Dosage Forms and Drug Delivery Systems,* Sixth Edition (Malvern, Pa.: Lea & Febiger, 1995). The components of the drug delivery device, e.g., canister, housing, metering valve, etc., are commercially available. For example many components are available from 3M Corporation, St. Paul, Minn. Typically, although not necessarily, the amount of formulation that is released per actuation of the drug delivery device is about 5 $\mu$g to about 100,000 $\mu$g of formulation.

Utility and Administration

The invention also provides a method for treating a patient suffering from a condition that is responsive to treatment with pulmonary administration of a bronchodilator. The method involves administering to the patient, via inhalation, the pharmaceutical formulation of the present invention. Although the method may be used to treat any condition, disease or disorder that can be remedied or prevented by the administration of a bronchodilator, the present method is advantageous for treating patients suffering from asthma, bronchitis, bronchospasm, emphysema, and any combination thereof. It is particularly preferred, however, that the method is used to treat patients suffering from asthma.

The formulations described herein have many advantages. The formulations can be used in conventional metered-dose inhalers. Furthermore, the formulations do not clog any part of the drug delivery device, e.g., valve, and address environmental concerns over the use of CFCs. Surfactants, solvents and cosolvents are essentially not present, thereby minimizing unpleasant tastes associated with these components and/or reducing extraction of any elastomeric components, e.g., gaskets, which may be present in the delivery system. Importantly, the effective absence of surfactants, solvents and cosolvents in the formulation has the added benefit that asthma attacks triggered by these components are substantially decreased or eliminated entirely.

As stated previously, the actual amount of the active agent to be administered will depend upon the age, weight, and general condition of the subject, the severity of the condition being treated, and the judgment of the prescribing physician or attending clinician. Therapeutically effective amounts will be known to those skilled in the art and/or are described in the pertinent reference texts and literature. An effective amount of the formulation may be administered with a single actuation (as measured from the mouthpiece) of the drug delivery device, i.e., inhaler. Alternatively, the effective amount may be administered through two, three, four or more actuations. Ideally, either one or two actuations will deliver an effective amount of active agent. Generally, the effective amount will range from about 1 $\mu$g to about 100 $\mu$g, more preferably from about 5 $\mu$g to about 75 $\mu$g, and most preferably about 10 $\mu$g to about 60 $\mu$g of the active agent. When the active agent is ipratropium bromide, it is preferred that each activation releases about 15 $\mu$g to about 25 $\mu$g of the bromide salt, and that two actuations (about 30 $\mu$g to about 60 $\mu$g of ipratropium bromide) are used to administer a therapeutically effective amount.

Administration of an effective amount may take place once, twice, three times or four times daily. Alternatively, or in addition to regularly schedule doses, administration may take place as needed or required by the patient. The total daily dose, however, should not exceed about 2,000 $\mu$g of the active agent. Preferably, the effective amount is administered four times daily, particularly for ipratropium bromide either alone or in combination with albuterol, e.g., albuterol sulfate.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entireties.

Experimental

The practice of the invention will employ, unless otherwise indicated, conventional techniques of pharmaceutical formulation and the like, which are within the skill of the art. Such techniques are fully explained in the literature. See, for example, *Remington: The Science and Practice of Pharmacy,* supra.

In the following examples, efforts have been made to ensure accuracy with respect to numbers used (e.g., amounts, temperature, etc.) but some experimental error and deviation should be accounted for. Unless indicated otherwise, temperature is in degrees C and pressure is at or near atmospheric pressure at sea level. All reagents were obtained commercially unless otherwise indicated.

EXAMPLE 1

An ipratropium bromide inhaler was prepared as follows. Bulk ipratropium bromide was processed into substantially nonacicular particles from its original needle-shaped particles using conventional milling techniques. Approximately 5.5 mg of the prepared ipratropium bromide was placed into an empty 19 ml aluminum can that was obtained from Presspart, Inc. (Cary, N.C.). A 25 µl valve (product code BK357, 20 mm, obtained from Bespak, Inc., Apex, N.C.) was crimped onto the aluminum using a crimping and pressure filling machine (Pamasol P 2005 machine, Pfaffikon, Switzerland). The filling head was then set to deliver approximately 8.3 g of 1,1,1,2-tetrafluoroethane (HFC-134a), available as DYMEL® 134a propellant (pharmaceutical grade) from E. I. du Pont de Nemours & Co., Wilmington, Del. The propellant was dispensed into the aluminum can using the crimping and pressure filling machine. The filled aluminum can was then was placed into an actuator (0.33 mm orifice actuator, Bespak, Inc., Apex, N.C.) ensuring that the stem of the valve was properly fitted into the internal spray orifice of the actuator. Upon repeated actuation, the inhaler delivered about 20 µg of the active agent per dose without clogging.

EXAMPLE 2

An ipratropium bromide inhaler is prepared following the procedure of Example 1, except that the amounts of the prepared ipratropium bromide and 1,1,1,2-tetrafluoroethane are changed. Ipratropium bromide is added to the canister in a range from about 4.9 to about 6.0 mg. The propellant, e.g., 1,1,1,2-tetrafluoroethane, is added to the canister in a range from about 7.5 to about 8.5 g. The inhaler delivers a therapeutically effective amount of the active agent without clogging, even upon repeated actuation.

We claim:

1. A pharmaceutical aerosol formulation, comprising:
   substantially nonacicular particles of a bronchodilator selected from the group consisting of ipratropium and pharmacologically acceptable salts, solvates, hydrates, esters and isomers thereof; and
   a propellant selected from the group consisting of a perfluorocarbon propellant, a hydrogen-containing fluorocarbon propellant, and mixtures thereof,
   wherein the formulation is substantially free of both surfactant and solvent.

2. The formulation of claim 1, wherein the bronchodilator is a pharmacologically acceptable salt of ipratropium.

3. The formulation of claim 2, wherein the pharmacologically acceptable salt of ipratropium is ipratropium bromide.

4. The formulation of claim 3, wherein the ipratropium bromide is in racemate form.

5. The formulation of claim 3, wherein the ipratropium bromide is levorotatory in enantiomerically pure form.

6. The formulation of claim 3, wherein the ipratropium bromide is dextrorotatory in enantiomerically pure from.

7. The formulation of claim 3, wherein the ipratropium bromide is in monohydrate form.

8. The formulation of claim 1, wherein the substantially nonacicular particles have an average particle size in the range of about 0.5 µm to about 10 µm.

9. The formulation of claim 7, wherein the average particle size is in the range of about 1 µm to about 7.5 µm.

10. The formulation of claim 9, wherein the average particle size is in the range of about 1 µm to about 5 µm.

11. The formulation of claim 1, wherein the substantially nonacicular particles are substantially spherical particles.

12. The formulation of claim 11, wherein the substantially spherical particles have an average particle size in the range of about 0.5 µm to about 10 µm.

13. The formulation of claim 12, wherein the average particle size is in the range of about 1 µm to about 7.5 µm.

14. The formulation of claim 13, wherein the average particle size is in the range of about 1 µm to about 5 µm.

15. The formulation of claim 1, wherein the propellant is a perfluorocarbon propellant.

16. The formulation of claim 15, wherein the perfluorocarbon propellant is selected from the group consisting of $CF_3CF_3$, $CF_3CF_2CF_3$ and mixtures thereof.

17. The formulation of claim 1, wherein the propellant is a hydrogen-containing fluorocarbon propellant.

18. The formulation of claim 17, wherein the hydrogen-containing fluorocarbon propellant is selected from the group consisting of $CHF_2CHF_2$, $CF_3CH_2F$, $CHF_2CH_3$, $CF_3CHFCF_3$ and mixtures thereof.

19. The formulation of claim 18, wherein the hydrogen-containing fluorocarbon propellant is selected from the group consisting of $CF_3CH_2F$, $CF_3CHFCF_3$ and mixtures thereof.

20. The formulation of claim 19, wherein the hydrogen-containing fluorocarbon propellant is $CF_3CH_2F$.

21. The formulation of claim 1, further comprising an additional active agent.

22. The formulation of claim 21, wherein the additional active agent is selected from the group consisting of an additional bronchodilator, an anti-inflammatory steroid and combinations thereof.

23. The formulation of claim 22, wherein the additional active agent is an additional bronchodilator.

24. The formulation of claim 23, wherein the additional bronchodilator is selected from the group consisting of albuterol, aminophylline, bitolterol, dyphylline, ephedrine, fenoterol, formoterol, isoetharine, isoproterenol, isoprenaline, metaproterenol, oxtriphylline, phenylephrine, pentoxifylline, pirbuterol, reproterol, rimiterol, salmeterol, theophylline, terbutaline, tolubuterol, orciprenaline, pharmacologically acceptable salts thereof and combinations thereof.

25. The formulation of claim 24, wherein the additional bronchodilator is albuterol.

26. The formulation of claim 25, wherein the additional bronchodilator is albuterol sulfate.

27. The formulation of claim 22, wherein the additional active agent is an anti-inflammatory steroid.

28. The formulation of claim 27, wherein the anti-inflammatory steroid is selected from the group consisting of beclomethasone, budesonide, cortisone, dexamethasone, flunisolide, hydrocortisone, prednisolone, prednisone, triamcinolone, pharmacologically acceptable salts thereof and combinations thereof.

29. A method for treating a patient suffering from a condition that is responsive to treatment with an aerosol formulation of a bronchodilator by administering, via inhalation, a therapeutically effective amount of a formulation comprising:
   substantially nonacicular particles of a bronchodilator selected from the group consisting of ipratropium and pharmacologically acceptable salts, solvates, hydrates, esters and isomers thereof; and
   a propellant selected from the group consisting of a perfluorocarbon propellant, a hydrogen-containing fluorocarbon propellant, and mixtures thereof, wherein the formulation is substantially free of both surfactant and solvent.

30. The method of claim 29, wherein the bronchodilator is a pharmacologically acceptable salt of ipratropium.

31. The method of claim 30, wherein the pharmacologically acceptable salt of ipratropium is ipratropium bromide.

32. The method of claim 31, wherein the ipratropium bromide is in racemate form.

33. The method of claim 31, wherein the ipratropium bromide is levorotatory in enantiomerically pure form.

34. The method of claim 31, wherein the ipratropium bromide is dextrorotatory in enantiomerically pure from.

35. The method of claim 31, wherein the ipratropium bromide is in monohydrate form.

36. The method of claim 29, wherein the substantially nonacicular particles have an average particle size in the range of about 0.5 $\mu$m to about 10 $\mu$m.

37. The method of claim 36, wherein the average particle size is in the range from about 1 $\mu$m to about 7.5 $\mu$m.

38. The method of claim 35, wherein the average particle size is in the range of about 1 $\mu$m to about 5 $\mu$m.

39. The method of claim 29, wherein the substantially nonacicular particles are substantially spherical particles.

40. The method of claim 39, wherein the substantially spherical particles have an average particle size in the range of about 0.5 $\mu$m to about 10 $\mu$m.

41. The method of claim 40, wherein the average particle size is in the range of about 1 $\mu$m to about 7.5 $\mu$m.

42. The method of claim 41, wherein the average particle size is in the range of about 1 $\mu$m to about 5 $\mu$m.

43. The method of claim 29, wherein the propellant is a perfluorocarbon propellant.

44. The method of claim 43, wherein the perfluorocarbon propellant is selected from the group consisting of $CF_3CF_3$, $CF_3CF_2CF_3$ and mixtures thereof.

45. The method of claim 29, wherein the propellant is a hydrogen-containing fluorocarbon propellant.

46. The method of claim 45, wherein the hydrogen-containing fluorocarbon propellant is selected from the group consisting of $CHF_2CHF_2$, $CF_3CH_2F$, $CHF_2CH_3$, $CF_3CHFCF_3$ and mixtures thereof.

47. The method of claim 46, wherein the hydrogen-containing fluorocarbon propellant is selected from the group consisting of $CF_3CH_2F$, $CF_3CHFCF_3$ and mixtures thereof.

48. The method of claim 47, wherein the hydrogen-containing fluorocarbon propellant is $CF_3CH_2F$.

49. The method of claim 29, wherein the formulation further comprises an additional active agent.

50. The method of claim 49, wherein the additional active agent is selected from an additional bronchodilator, an anti-inflammatory steroid and combinations thereof.

51. The method of claim 50, wherein the additional active agent is an additional bronchodilator.

52. The method of claim 51, wherein the additional bronchodilator is selected from the group consisting of albuterol, aminophylline, bitolterol, dyphylline, ephedrine, fenoterol, formoterol, isoetharine, isoproterenol, isoprenaline, metaproterenol, oxtriphylline, phenylephrine, pentoxifylline, pirbuterol, reproterol, rimiterol, salmeterol, theophylline, terbutaline, tolubuterol, orciprenaline, pharmacologically acceptable salts thereof and combinations thereof.

53. The method of claim 52, wherein the additional bronchodilator is albuterol.

54. The method of claim 53, wherein the additional bronchodilator is albuterol sulfate.

55. The method of claim 50, wherein the additional active agent is an anti-inflammatory steroid.

56. The method of claim 55, wherein the anti-inflammatory steroid is selected from the group consisting of beclomethasone, budesonide, cortisone, dexamethasone, flunisolide, hydrocortisone, prednisolone, prednisone, triamcinolone, pharmacologically acceptable salts thereof and combinations thereof.

57. The method of claim 29, wherein the therapeutically effective amount is about 1 $\mu$g to about 100 $\mu$g.

58. The method of claim 57, wherein the therapeutically effective amount is about 5 $\mu$g to about 75 $\mu$g.

59. The method of claim 58, wherein the therapeutically effective amount is about 10 $\mu$g to about 60 $\mu$g.

60. The method of claim 59, wherein the therapeutically effective amount is about 30 $\mu$g to about 60 $\mu$g.

61. The method of claim 29, wherein the condition is asthma, bronchitis, bronchospasm or emphysema.

62. The method of claim 61, wherein the condition is asthma.

63. A drug delivery device comprising:
   a sealed canister having a metering valve and containing a pharmaceutical aerosol formulation comprised of substantially nonacicular particles of a bronchodilator selected from the group consisting of ipratropium and pharmacologically acceptable salts, solvates, hydrates, esters and isomers thereof, and a propellant selected from the group consisting of a perfluorocarbon propellant, a hydrogen-containing fluorocarbon propellant, and mixtures thereof, wherein the sealed canister has a head space of greater than about 15% and less than about 98% based on the total volume of the sealed canister and wherein the formulation is substantially free of both surfactant and solvent; and
   a housing adapted to hold the canaster.

64. The device of claim 63, wherein the device is a metered-dose inhaler.

65. The device of claim 63, wherein the head space is greater than about 20% and less than about 98% based on the total volume of the sealed canister.

66. The device of claim 65, wherein the head space is greater than about 40% and less than about 98% based on the total volume of the sealed canister.

67. The device of claim 66, wherein the head space is greater than about 60% and less than about 98% based on the total volume of the sealed canister.

* * * * *